United States Patent [19]

Swift

[11] Patent Number: 4,472,822
[45] Date of Patent: Sep. 18, 1984

[54] X-RAY COMPUTED TOMOGRAPHY USING FLYING SPOT MECHANICAL SCANNING MECHANISM

[75] Inventor: Roderick D. Swift, Belmont, Mass.

[73] Assignee: American Science and Engineering, Inc., Cambridge, Mass.

[21] Appl. No.: 395,943

[22] Filed: Jul. 7, 1982

Related U.S. Application Data

[63] Continuation of Ser. No. 150,823, May 19, 1980, abandoned.

[51] Int. Cl.³ .............................................. G03B 41/16
[52] U.S. Cl. ..................................... 378/10; 378/19; 378/146; 378/17
[58] Field of Search ................ 378/178, 10, 179, 146, 378/20, 19, 17

[56] References Cited

U.S. PATENT DOCUMENTS

| Re. 28,544 | 9/1975 | Stein et al. | 378/146 |
|---|---|---|---|
| 3,432,660 | 3/1969 | Anger | 378/17 |
| 4,084,094 | 4/1978 | Froggatt | 378/10 |
| 4,099,060 | 7/1978 | Franke | 378/146 |
| 4,132,895 | 1/1979 | Froggatt | 378/146 |
| 4,174,481 | 11/1979 | Liebetruth | 378/20 |
| 4,242,583 | 12/1980 | Annis et al. | 378/146 |
| 4,316,091 | 2/1982 | Bernardi | 378/197 |
| 4,422,177 | 12/1983 | Mastronardi et al. | 378/20 |

FOREIGN PATENT DOCUMENTS

| 2732073 | 1/1978 | Fed. Rep. of Germany | 378/13 |
|---|---|---|---|
| 1528574 | 10/1978 | United Kingdom | 378/19 |

Primary Examiner—Alfred E. Smith
Assistant Examiner—Carolyn E. Fields
Attorney, Agent, or Firm—Pollock, Vande Sande and Priddy

[57] ABSTRACT

A radiant energy imaging apparatus for obtaining CT scans employs an X-ray unit operative to produce a pencil beam of X-ray radiant energy which is caused to scan in a horizontal plane through an angle, sufficiently great to embrace a cross section of a human body being examined, along a single, elongated, horizontally oriented detector forming a portion of the X-ray unit and located on the side of the body opposite to an X-ray source in the unit. A supporting structure, adapted to be rotated about a vertical axis, supports a human body in a vertical orientation; and when the system is scanning in the CT mode, the supporting structure rotates the human body smoothly and continuously about a vertical axis while the X-ray unit is held at a fixed position adjacent a horizontal section of interest of the human body. In addition to being used as a CT scanner, the system can be used to generate its own localization images and to perform digital radiography on those images and can be employed in this mode of operation to obtain anterior-posterior, lateral or oblique images at any desired angle. In addition, when used as a CT scanner, the apparauts can be provided with several contiguous linear detectors all of which are associated with the same scanning beam, so that several CT scans are generated simultaneously. The effective slice width of a particular region of interest can be adjusted by combining the outputs of one or more detectors in a contiguous group.

7 Claims, 5 Drawing Figures

X-RAY COMPUTED TOMOGRAPHY USING FLYING SPOT MECHANICAL SCANNING MECHANISM

This is a continuation of application Ser. No. 150,823, filed May 19, 1980, now abandoned.

BACKGROUND OF THE INVENTION

Systems have been suggested heretofore for obtaining computed tomography (CT) scans for medical or other purposes. In general, these known systems are comparatively complex structurally, very expensive, and tend to subject a patient to a comparatively high dosage level of radiation if X-ray images of adequate quality to effect an X-ray diagnosis are to be obtained. The present invention is concerned with the provision of an apparatus which, when employed as a CT scanner, is capable of producing X-ray images which are comparable to and in some cases better than those produced by present-day commercial CT equipment, and which achieve these results at far less cost and by subjecting the patient to a far smaller level of dosage than is customary at the present time. These advantages are achieved by the provision of equipment which employs a mechanical scanner, of the general type described in Stein et al U.S. Pat. No. Re. 28,544 (originally U.S. Pat. No. 3,780,291) which is operative to produce a pencil beam of X-rays that scans a single efficient detector.

CT equipments employing flying spot scanning techniques have been suggested heretofore. One such arrangement is described, for example, in an article entitled "Low-Dosage X-Ray Imaging System Employing Flying Spot X-Ray Microbeam (Dynamic Scanner)" by Tateno and Tanaka, Radiology 121: October 1976, pp 189-195. The Tateno et al system, although described as being capable of achieving quality X-ray images at lower dosages than are customarily employed in CT equipment, uses a special noncommercial X-ray tube characterized by sophisticated electron optics analogous to those employed in high voltage electron microscopes and electron beam machining equipment, relies on an electronic scanning technique, and contemplates the use of a two-dimensional detector. These characteristics of this previously-described system make the system far more expensive than the system of the present invention, which utilizes an extremely simple mechanical scanning arrangement. In addition, inasmuch as the Tateno et al system employs a two-dimensional detector, it is incapable of rejecting scattered radiation, in contrast to the system of the present invention wherein, by use of a single, efficient one-dimensional detector, such rejection is automatically accomplished.

Further advantages accrue to the present invention, as compared to the scanning techique of Tateno et al which employs a device that produces a flying-spot X-ray beam by "pinhole" projection of an electronically scanned focal spot in the X-ray tube. In order to produce an X-ray field large enough to subtend a patient cross-section for a CT scan, the beam must diverge over a considerable distance from the pinhole collimator. The required distance is equivalent to locating the pinhole at the focal spot (X-ray source) of the present invention. Since the beam cross-section at any point represents a pinhole image of the focal spot, the relatively large distance from pinhole collimator to patient results in a relatively large beam cross-section, with a concurrent loss of resolution. The close proximity of the collimation systems to the patient in the present invention is an important improvement, since the beam size is essentially a projection of the small collimator apertures from a distant source.

Another system suggested heretofore, for producing CT images by use of a flying spot technique, is described in Hounsfield U.S. Pat. No. 3,866,047 for "Penetrating Radiation Examining Apparatus Having A Scanning Collimator". The Hounsfield apparatus contemplates the provision of a mechanical scanning device comprising a pair of elongated shutters which are mounted for mechanical reciprocation in synchronism with one another. Each shutter member is provided with a plurality of slots which coact with one another to produce a plurality of angularly spaced radiation beams simultaneously, each beam being caused to scan through a comparatively small angle onto a comparatively small detector which is associated with that beam. The Hounsfield reciprocating shutter arrangement is far more complex mechanically than the comparatively simple rotating collimator which is employed in the present invention, and requires critical alignments of the plural slots which are utilized in the spaced shutters of the Hounsfield mechanical scanner. Moreover, since Hounsfield contemplates the simultaneous generation of a plurality of angularly displaced X-ray beams, and the simultaneous scanning of all of those beams across a like plurality of detectors, the arrangement poses problems of possible loss of data at the boundaries between adjacent detectors. Two specific problems may be identified: (1) The boundaries produce a geometric inefficiency which results in wasted dose to the patient, and (2) The missing information along the beam paths through the boundaries can result in artifacts in the reconstructed CT image.

Further problems with the multiple beam arrangement of Hounsfield are related to the need for accurate matching or normalization of the plural detectors over the full dynamic range of the signal, without which severe artifacts can result in the reconstructed image. A number of phenomena, as for example cathode resistivity and dynode fatigue, are known to produce nonlinearities and gain changes in photomultiplier tubes, the use of which is contemplated by Hounsfield. Similar problems may occur with other plural detectors which are less efficient than the scintillator-photomultiplier combination. In order to reduce the dynamic range, and thereby alleviate the normalization, Hounsfield has incorporated a "plastics block" (item 26 in his Figures) and suggests the use of a water bag filling the space between the plastics block and the patient. The use of such devices introduces extra expense and mechanical complexity, and results in wasted dose because of photon absorption (and consequent loss of information) between the patient and the detector.

The present invention utilizes a single, efficient detector and a simple mechanical scanning arrangement to obviate all these problems of the prior art.

SUMMARY OF THE INVENTION

The radiant energy imaging apparatus of the present invention comprises an X-ray system adapted to be moved rotationally as a unit about a support structure which is provided to support a body or other object to be examined by means of penetrating radiation. The X-ray unit comprises a source of X-rays located on one side of the support means, a single elongated radiant energy detector located on the opposite side of the support means and extending in a direction transverse to the axis of rotation of the X-ray system, and a mechanical scanning device located between the X-ray source and the support means for configuring radiation emitted by the source into a single pencil beam of X-rays, and for scanning that single pencil beam along the direction of elongation of the single detector through an angle which is sufficiently large to subtend a complete cross section of a body or object on the support means. The mechanical scanning device is of the general type described in Stein et al U.S. Pat. No. Re. 28,544 reissued Sept. 2, 1975, on the basis of U.S. Pat. No. 3,780,291 issued Dec. 18, 1973, and comprises a first collimator for shaping radiation emitted by an X-ray source into a fan-shaped beam of X-rays, and a second collimator comprising a disc-shaped chopper wheel fabricated of a radiation opaque material and having one or more X-ray transparent slots therein through which a pencil beam of X-rays can pass, said pencil beam being scanned along said single linear detector as the second collimator rotates. The chopper disc can take the form shown in the aforementioned Stein et al patent or, in the alternative, it can comprise a drum-shaped structure of the type shown in Jacob U.S. Pat. No. 4,031,401. Each of these patents is assigned to American Science and Engineering, Inc., Cambridge, Mass., the assignee of the present invention.

The X-ray system, comprising the X-ray source, mechanical scanning device, and single elongated detector, is adapted to be moved in various directions for various different purposes. The system may be moved, for example, in translation along a line parallel to the axis of the support means to provide conventional radiographic projection in a manner analogous to that achieved by the Medical MICRO-DOSE ® X-Ray system manufactured by American Science and Engineering, Inc., Cambridge, Mass. In this mode of operation, because of the fact that the X-ray system is adapted to be rotated through any desired angle relative to the body support structure, images can be readily obtained as AP, PA, lateral or oblique images at any desired angle.

The mode of operation described above can also be employed to produce localization images preparatory to the CT scanning operation, i.e., the X-ray system may be translated as a unit parallel to the axis of the body support structure, and the conventional images obtained during this mode of operation can be monitored to localize the system at a particular region of the body where a CT slice is to be taken, whereafter the X-ray system is caused to effect a continuous substantially constant speed of rotation relative to the body support structure to obtain a CT scan of the selected slice. This relative rotation between the scanner and the object being examined can be achieved by rotating either the scanning mechanism, the object, or both. The axis of relative rotation may, moreover, be selected for any desired applications, and may be either horizontal, vertical, or at a selected angle therebetween.

The system preferably includes means for adjusting the size of the CT scan field, either by mechanical manipulation of the fan beam and chopper wheel collimation system, or by displacing the position of the X-ray unit or selected portions thereof relative to the axis of rotation so as to vary the spacing between said axis of rotation and the X-ray source and/or detector.

The system can also be used to generate several CT scans simultaneously by using one or more fan beam collimation slits, all of which are traversed simultaneously, for example, by a slit in a rotating chopper wheel, and by directing a plurality of parallel flying-spot beams or a single beam of sufficient dimensions onto several contiguous linear detectors. The multiple detectors used in this configuration, wherein each elongated detector subtends more than the full field of its CT cross-section, are not subject to the same severe normalization problems that were described with respect to the plural detectors in the aforementioned Hounsfield patent. This is because (a) each CT slice is obtained by a single detector and (b) each detector can be calibrated many times during a single CT scan by using data obtained when the flying spot beam impinges on the detector outside the circle of its CT image field. The outputs of several detectors can be employed to produce a plurality of independent CT images simultaneously, thereby reducing the time otherwise required to generate a series of CT images of one patient. This ability may be particularly useful for the generation of so-called sagittal and coronal reconstructions from multiple slice data, inasmuch as obtaining the data simultaneously obviates any problems related to motion of the patient between successive scans. In an alternative mode of operation, the outputs of two or more detectors in a contiguous group can be combined to effectively adjust the width of a single slice under examination.

BRIEF DESCRIPTION OF THE DRAWINGS

The foregoing objects, advantages, construction and operation of the present invention will become more readily apparent from the following description and accompanying drawings wherein.

DESCRIPTION OF THE PREFERRED EMBODIMENTS

As described previously, the present invention is concerned with a radiant energy imaging apparatus for obtaining CT scans and other types of scan for medical and other purposes. It is based on the scanning mechanism and the single efficient detector employed in the Medical MICRO-DOSE ® X-ray system manufactured by American Science and Engineering, Inc., Cambridge, Mass. That prior system is illustrated in FIG. 1 of the drawings.

Figure 1:
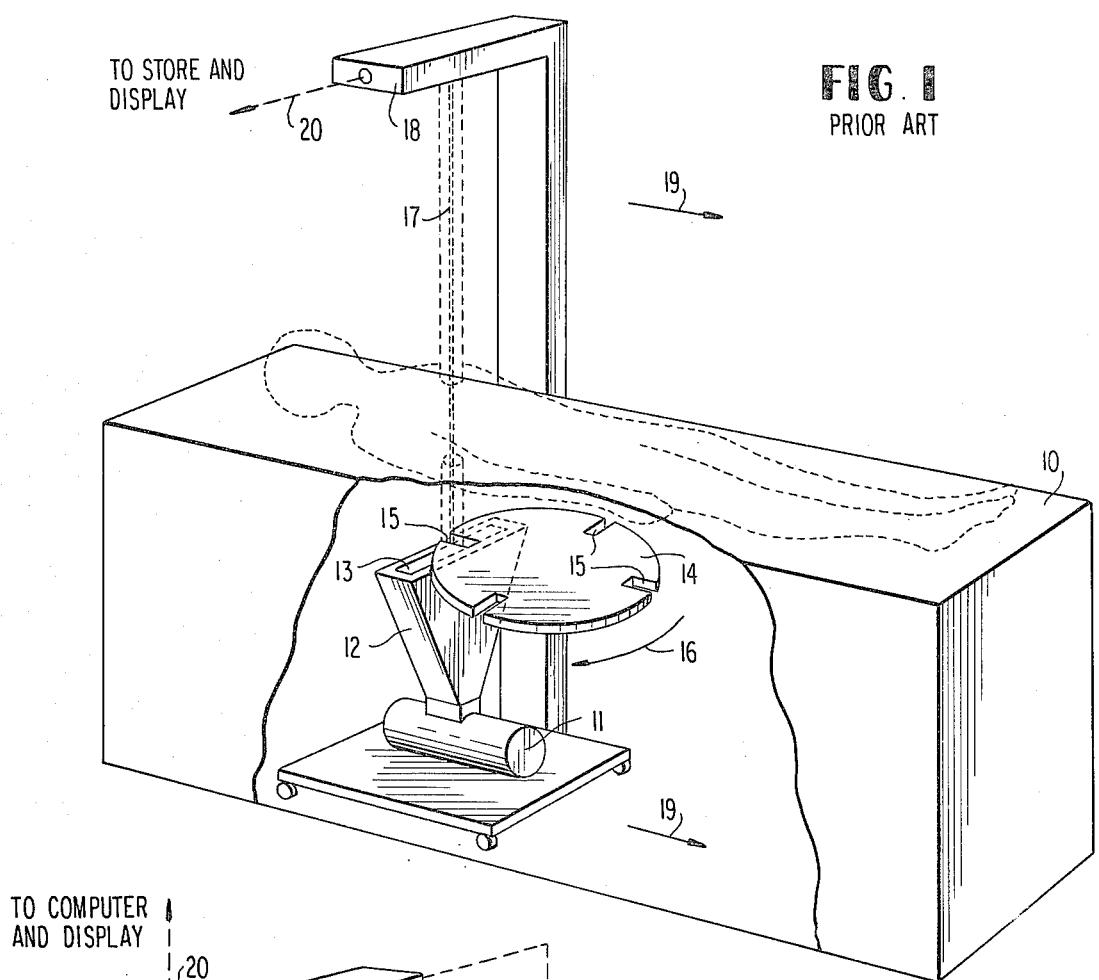
FIG. 1 is a diagrammatic illustration of a prior art Medical MICRO-DOSE ® X-ray system.

The apparatus shown in FIG. 1 comprises a table or support structure 10 adapted to support the body of a patient who is to be examined by means of penetrating radiation, and an associated X-ray system adapted to produce a pencil beam of X-rays which is caused to scan across the patient's body. The X-ray system corresponds in general to the system which is shown in Stein et al U.S. Pat. No. Re. 28,544, the disclosure of which is incorporated herein by reference, and comprises a conventional rotating anode X-ray tube 11 whose output is collimated into a narrow fan beam by means of a wedge-shaped collimator 12, fabricated for example as a composite of lead and tungsten, having an elongated comparatively narrow opening 13 at its upper end. The fan beam is further collimated by an X-ray opaque chopper wheel 14, fabricated for example of lead-filled aluminum with tungsten jaws, that is provided with a plurality of slits 15 extending radially inwardly from the outer edge of said wheel 14. The chopper wheel 14 is mounted for rotation about a central axis as indicated by arrow 16, and is so positioned that an edge of the wheel overlies and completely covers slot 13 in collimator 12, except for the region of overlap of the slits 13, 15. For purpose of illustration, i.e., in order that the slot 13 may be more readily seen in FIGS. 1 and 2, this completely overlying relationship has not been shown in said figures, and reference is accordingly made to the drawings in Stein et al U.S. Pat. Re. 28,544 in this respect.

The lead and tungsten employed in collimators 12, 14 fully attenuate X-rays except in the region of overlap of the slits and the motion of the wheel 14 causes the slits 15 to traverse the fan beam repeatedly, thereby generating a single scanning pencil beam of X-rays 17 whose cross sectional dimensions are determined by the shapes of slits 13 and 15 in their region of overlap. This pencil-X-ray beam is partially attenuated by the subject on support 10, and the unattenuated X-rays are absorbed by an elongated photon detector 18, comprising a single efficient detector of the type described in the aforementioned Stein et al patent, as the pencil beam 17 scans from a position adjacent one end of detector 18 toward a position adjacent the other end thereof. During this scanning operation, the entire X-ray system, including the X-ray source, the chopper wheel, and the detector, is moved as a unit in the direction indicated by arrows 19, i.e., in a direction transverse to the direction of elongation of detector 18, along the length of the patient, who remains stationary on table 10, to produce multiple rows of data in the nature of a TV raster which data is supplied from detector 18, as at 20. These output signals produce a radiograph on the video (TV) monitor (not shown) e.g., by intensity modulating the CRT electron beam on a storage oscilloscope, or on a scan converter storage tube of known type. Alternatively, the output signals may be digitized and stored in a computer accessible memory, and processed by computer to produce a digital radiograph on a video monitor or other display device.

The signal detector 18 is a scintillation crystal coupled to one or more photomultipliers whose outputs are combined, and nerly 100% of the X-rays which are not attenuated by the patient are detected. The electrical signals obtained at the output of the photomultipliers are pulses, with the amplitude of each pulse being proportional to the energy of a single detected X-ray photon. Since the rate of X-ray photons incident on the detector is large, these pulses add together to give a net signal which, at any instant of time, is proportional to the incident X-ray flux in the attenuated X-ray pencil beam. The electrical signal from the detector, during one scan of the pencil beam from one end of the detector to the other, corresponds to a one-dimensional radiographic line image of the object, analogous to one scan line on an ordinary television monitor. The second dimension of the image is generated by virtue of the motion of the source-collimator-detector plane with respect to the patient. The series of line images is sequentially stored in digital form and, after the X-ray exposure is complete, the radiographic data are read out line-by-line onto the television monitor. The readout is sequentially ordered in the same manner in which the data are read into storage so that the image on the monitor screen is the X-ray shadowgraph of the subject being examined.

Figure 2:
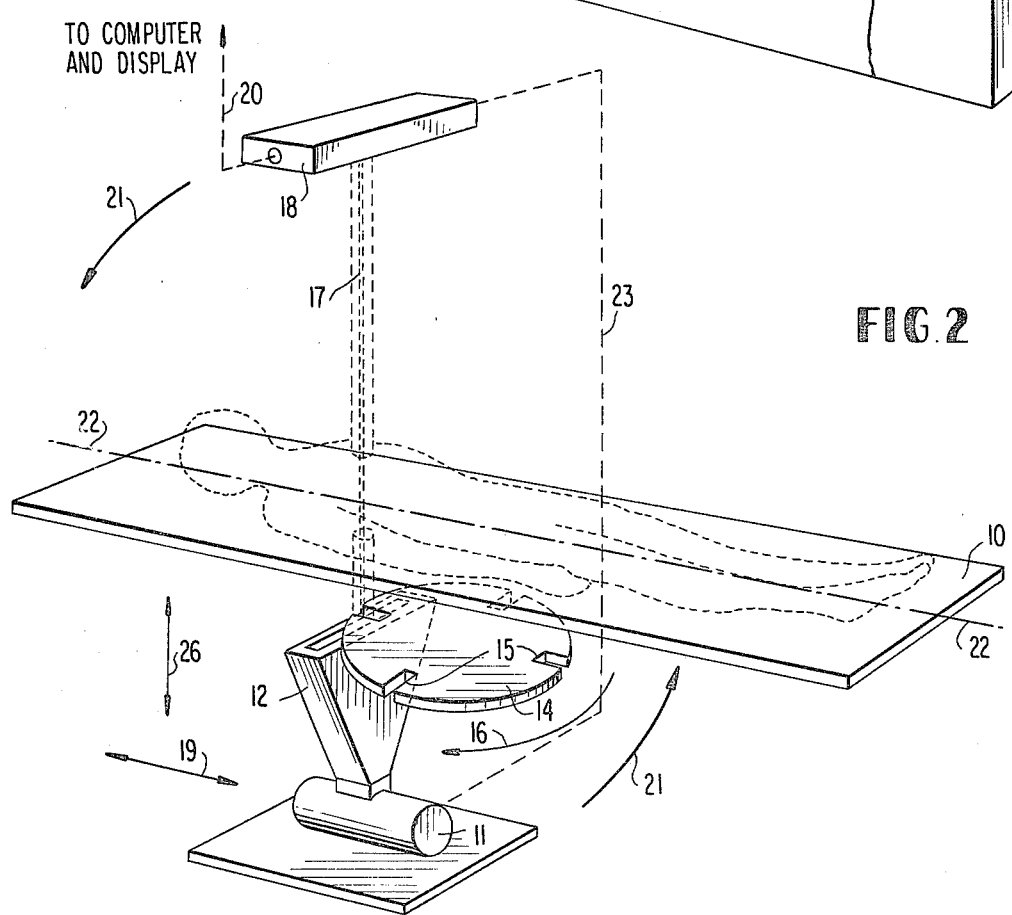
FIG. 2 is a diagrammatic illustration of the radiant energy imaging apparatus constructed in accordance with one embodiment of the present invention.

In the prior art apparatus shown in FIG. 1, the X-ray system is adapted to be moved in translation only, i.e., in the direction of arrows 19. However in accordance with the present invention, the X-ray system of FIG. 1, like parts of which are designated by like numerals in FIG. 2, is mounted to exhibit a variety of degrees of motion under the control of various drive means kown per se and therefore not shown in FIG. 2 for purposes of simplicity. The translateral motion indicated by arrow 19 may be retained in FIG. 2 when it is desired to have the system of the present invention exhibit the capabilities already described in reference to FIG. 1 and/or when the system of FIG. 2 is to provide CT scans preceded by the generation of localization images. Basically, however, the system of FIG. 2 is characterized by an arrangement wherein the translateral motion indicated by arrow 19 is replaced by or supplemented by a rotational motion of the patient relative to the scanner, as indicated by arrows 21, about an axis of rotation 22 which is the nominal axis of a patient supported on table 10. In practice, either the patient or the scanning mechanism, or both, may be rotated. When the scanning mechanism is to be rotated about axis 22, it is rotated as a unit, i.e., line detector 18 on one side of table 10 is physically connected to the X-ray generating mechanism and collimator structure on the other side of said table, by means of an appropriate interconnecting structure which is indicated by broken line 23.

When used as a CT scanner, the CT scan achieved by the system of FIG. 2 is essentially similar to that of so-called two motion, or translate-rotate, CT scanners, but without the usual mechanical disadvantages and complexities of known such devices which require reciprocating mechanical translations of X-ray source, collimator and detector(s) to take place between incremental rotational motions of the assembly. In the present invention, the two motions (sweeping beam and rotating scanning assembly) are performed smoothly, continuously and simultaneously. The number of traverses of the pencil beam during one rotation of the scanner relative to the patient establishes the number of "views" of the CT scan. The data read out from the detector 18 is reconstructed by methods well known in the CT art, e.g., appropriate algorithms are described in the article *Fan Beam Reconstruction Methods* by B. K. P. Horn, Proceedings IEEE, December 1979, pp. 1616–1623.

Figure 3:
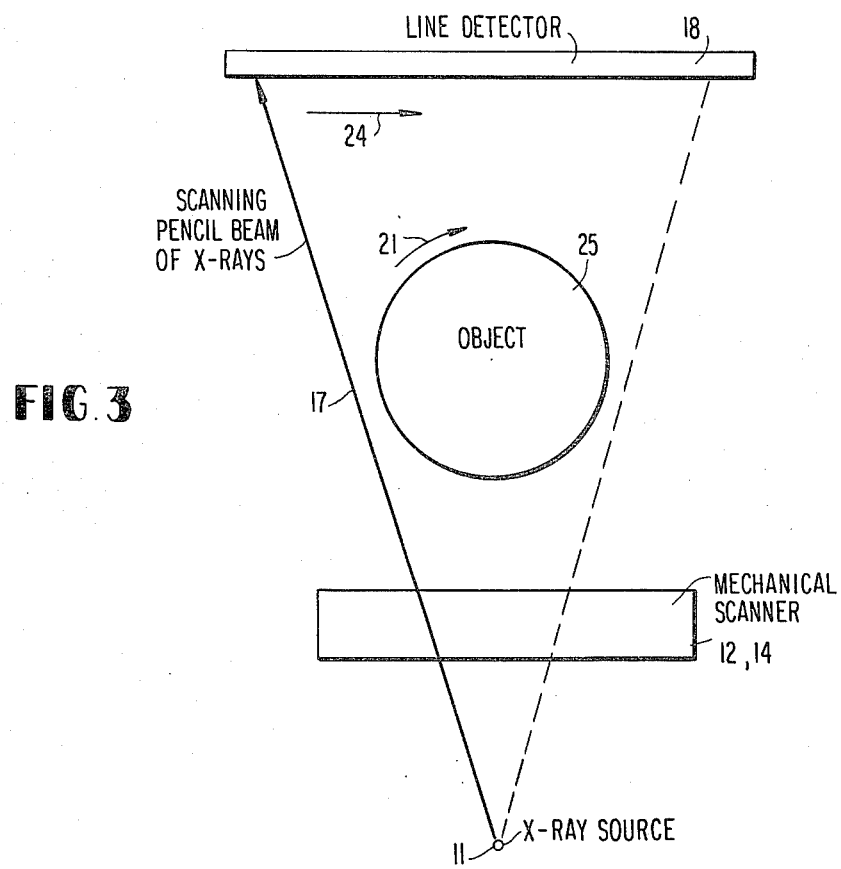
FIG. 3 illustrates the system of FIG. 2 used as a CT scanner.

One traverse of the beam along detector 18 typically takes approximately 1/180 seconds, and the typical rotation of the object being examined relative to the X-ray scanning system may be accomplished in approximately 5 to 10 seconds, giving a total of between 900 and 1800 views during a complete rotation of the X-ray scanner relative to the patient. These figures are given by way of example only, and in one embodiment of the invention the scan occurred at the rate of 30 scans per second, and the complete relative rotation of the scanning system and object being examined occurred in a time period of 15 seconds, to produce 450 views. The general operation of the system, in accordance with these aspects of the invention, is depicted in FIG. 3 wherein, again, like numerals are used to designate like parts. The significant points to note by reference to FIG. 3 are that the X-ray source 11 and mechanical scanner 12, 14 coact to produce a single scanning pencil beam of X-rays, which is scanned linearly in the direction of arrow 24 from one end to the other end of line detector 18, and which, in the course of this scanning operation, subtends an angle which embraces a complete cross section of the body or object generally designated 25 that is being moved rotationally (see arrow 21) relative to the X-ray scanner.

The size of the CT scan field can be adjusted by mechanical manipulation of the fan beam and chopper wheel collimation system 12, 14, i.e., by changing the slit sizes in the collimators. Alternatively, the field size can be adjusted (referring to FIG. 3) by moving the axis of rotation of object 25 closer to the source 11 thereby to effect a smaller field and a higher resolution, or by moving the axis of rotation closer to the detector 18 to achieve a larger field and a lower resolution. These possible movements of the X-ray source 11 and/or the detector 18 relative to table 10 have been designated in FIG. 2 by arrow 26.

Typically, the total dosage to which the scanned region of the body is exposed during the taking of a CT scan is approximately 100 mR. This dosage is from 1/10th to 1/100th of the dosage which occurs in present-day commercial CT scanners, but the picture which is achieved by the present invention at this very low dosage has nevertheless been found to be comparable to, and in certain respects better than, those which are achieved at far greater cost and at far higher dosages by present day commercial scanners. In addition to achieving these significant advantages, the present invention retains a number of the advantages of the prior art system shown in FIG. 1. More particularly, it achieves sub-millimeter spatial resolution, nearly total rejection of scattered radiation, and dose efficiency approaching 100%.

Another major advantage of the system shown in FIG. 2 is that it serves as its own localization system, and has the ability to perform digital data processing in either of two modes, i.e., it is a dual purpose, digital radiograph/CT system. Moreover, because of the relative rotation feature represented by arrows 21, the system can be used not only to generate its own localization images by moving the X-ray source and detector in translation relative to the patient as indicated by arrow 19, and to perform digital radiography on those images, but can readily obtain images as AP, PA, lateral or oblique images at any desired angle.

Figure 5:
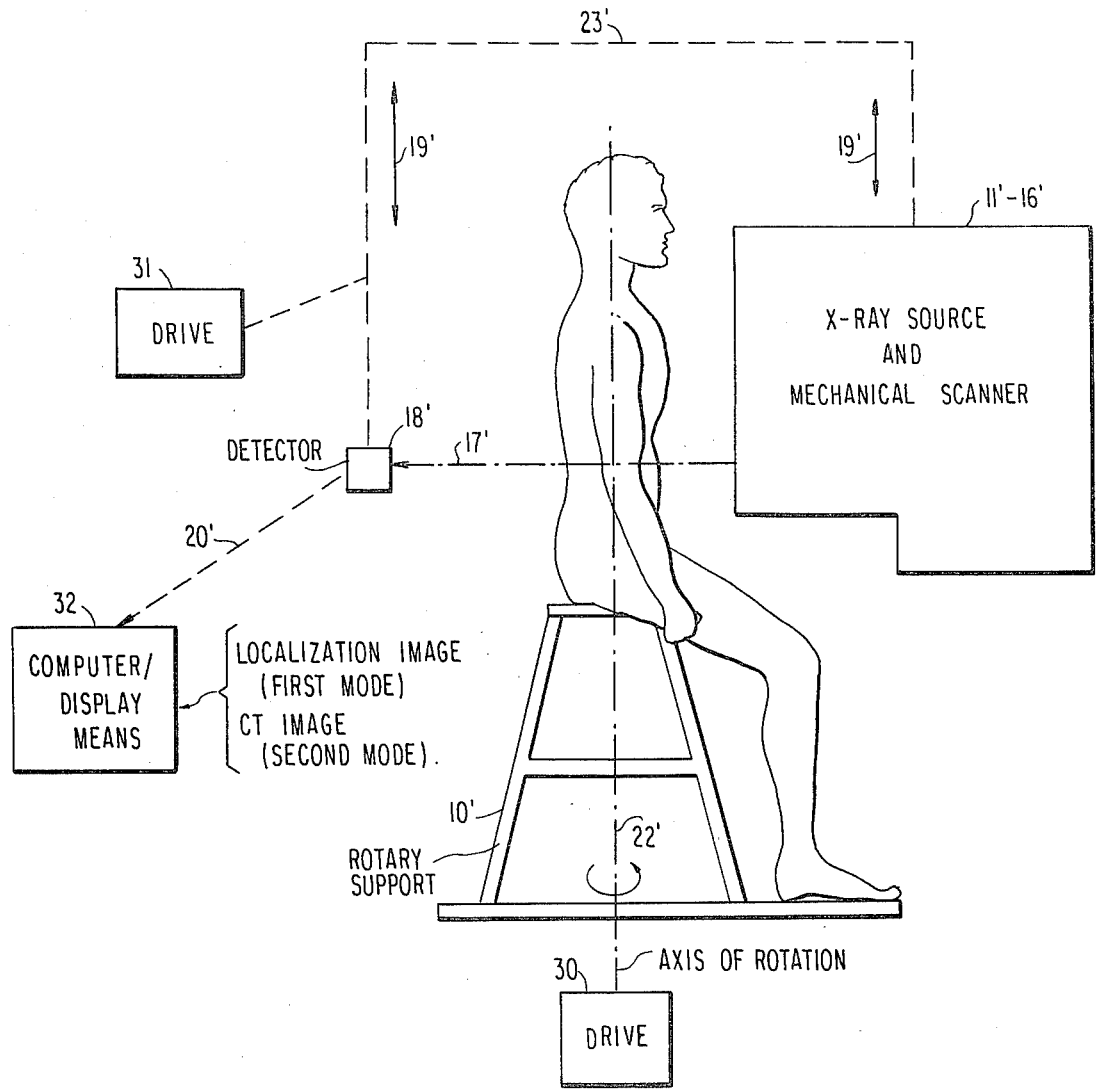
FIG. 5 is a diagrammatic illustration of the radiant energy imaging apparatus constructed in accordance with another embodiment of the present invention.

As indicated previously, the relative rotation between the object or patient and scanner may be achieved by rotating either the scanning mechanism, the object, or both. Moreover, the axis of rotation may be selected and oriented as desired for any prevailing application and, in particular, it may be horizontal as depicted in FIGS. 1 and 2, or vertical as shown in FIG. 5. A vertical orientation of the scan axis exhibits certain advantages.

The radiation source employed in the invention can be a conventional X-ray tube, or a radioisotope source, or a synchrotron. Regardless of the source employed, however, the simplifications which are accomplished by the present invention result in part from the use of a rotating type collimator which can take the form shown in the drawing, or the form described in Jacob U.S. Pat. No. 4,031,401, or which, if desired, can take the form of a rotating cylinder having helical radiation-transparent slots therein.

The detector employed has essentially 100% detection efficiency and 100% geometrical efficiency, unlike most CT scanner detector arrays. The spatial resolution of the CT image is high. Transverse resolution (in the plane of the slice) and axial resolution (slice thickness) are both sub-millimeter, and this resolution is achieved without sacrificing dose efficiency. Moreover, radiographic images and CT images may be obtained by locating detectors outside the plane of the scan, and then using the detected scattered radiation to generate an image, as is described for example in the aforementioned Stein et al patent. Such back scatter imaging is possible in the present invention since there is a single known geometric position of the scanning pencil beam at any instant of time, and the scatter from its path through the object principally controls the strength of the scattered signal at that time.

The system shown in FIG. 2 (and in FIG. 5, to be described) can be used moreover, to generate several CT scans simultaneously. This is accomplished by an arrangement of the type generally depicted in FIG. 4 wherein a plurality of line detectors such a 18a, 18b and 18c are disposed in side-by-side, parallel, contiguous relation to one another, and the pencil beam (shown in cross section 17a, in FIG. 4) is so dimensioned that it impinges on the plurality of detectors simultaneously as it is swept in the direction 24 from one end to the other of the contiguous detectors. The pencil beam 17a can comprise a plurality of parallel beams which are associated respectively with the detectors 18a–18c, or a single beam which is elongated in cross section in a direction transverse to the scan direction 24, and these beam configurations can be achieved by providing one or more fan beam collimation slits in the mechanical scanner 12, 14, or by increasing the width of the slot 13 in collimator 12, and correspondingly increasing the length of the slot 15 in collimator 14.

Figure 4:
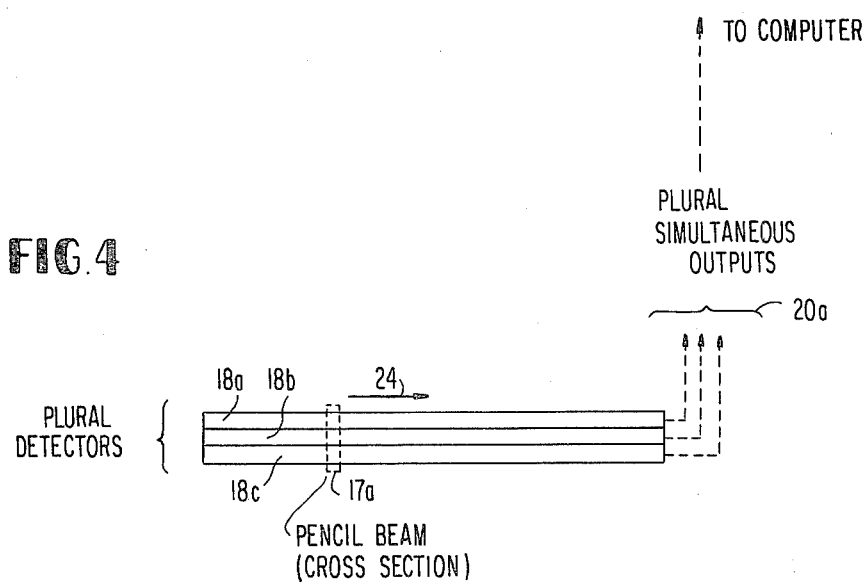
FIG. 4 is a diagrammatic illustration of a modified detector arrangement which can be employed in the arrangement of FIG. 2 to obtain multiple slice scans.

By using an arrangement of the type shown in FIG. 4, a plurality of outputs 20a are obtained simultaneously from the plural detectors 18a–18c, and these plural simultaneous outputs can be processed in varying fashions to achieve various different results. For example, the plural outputs may be processed individually to produce multiple slice pictures simultaneously. Alternatively, the outputs of two or more detectors in a contiguous group can be combined and processed thereby, in effect, to adjust the width of a particular slice being examined.

FIG. 5 shows a modified arrangement constructed in accordance with the present invention wherein the components shown in FIG. 2 are turned through 90° so that the patient is supported in a vertical, rather than a horizontal, orientation. Like elements are identified by like numerals, with however a prime notation being used in the arrangement of FIG. 5. In a first mode of operation, the patient support means 10' and the patient thereon are moved by drive means 30 about vertical axis 22' to a desired angle relative to the unit consisting of mechanically interconnected X-ray source/scanner 11'–16' and elongated horizontal detector 18', and then, while said relative angle is maintained and the support means 10' is in a nonrotating condition, the said unit is moved by drive means 31 in vertical translation (arrows 19') generally parallel to the vertical patient axis 22' to produce a localization image at computer/display means 32 representative of a vertical axial section of the patient. Then, in a second mode of operation, the unit 11'-16', 18' is positioned translationally by drive means 31 adjacent a particular corss-sectional portion of interest of the patient being examined, selected by reference to said localization image, whereafter the support 10' and the patient thereon are rotated smoothly and continuously by drive means 30 about the vertically oriented axis of rotation 22' while the unit 11'-16', 18' is held stationary thereby to produce, by means of computer/display means 32, a CT image representative of a horizontal slice of the patient.

The present invention lends itself to other techniques as well. For example, by using different filtering or detector characteristics for contiguous planes, or by using a low energy detector backed up by a high energy detector in the same plane, dual energy data may be obtained simultaneously. This may be used for either CT or digital radiographic images. The subtraction of two images taken with different energy responses can be used to emphasize iodinated contrast material. Utilizing this feature combined with multiple slices allows an image of, for example, blood vessels in a volume rather than a slice.

While I have thus described preferred embodiments of the present invention, it must be understood that the foregoing description is intended to be illustrative only and not limitative of the present invention. Many variations have already been described, and others will be apparent to those skilled in the art. For example, although the implementation of the invention has been described in connection with medical diagnostic imaging, the invention is also applicable to any nondestructive testing application. All such variations and modifications are intended to fall within the scope of the appended claims.

Having thus described my invention, I claim:

1. A radiant energy imaging apparatus for examining a human body by means of penetrating radiation, said apparatus comprising support means for supporting a human body to be examined and for rotating the human body about a vertically oriented axis of rotation, an X-ray system movable translationally as a unit in a vertical direction parallel to said axis of rotation; said X-ray system comprising a source of X-rays located entirely on one side of said support means, elongated radiant energy detector means located on the opposite side of said support means and extending in a horizontal direction transverse to said vertical axis of rotation, and a mechanical scanning device located entirely between said X-ray source and said support means for producing a single pencil beam of X-rays and for scanning said single pencil beam in a horizontal plane through a human body on said support means and along the horizontal direction of elongation of said detector; means the length of said elongated detector means and the positions of said detector means and mechanical scanning device being selected to cause said pencil beam of X-rays to subtend an angle which embraces a complete cross section of a human body on said support means as said pencil beam of X-rays is scanned horizontally along said detector means; drive means for selectively rotating said support means about its vertical axis of rotation and for selectively effecting vertical translational movement of said X-ray source, said mechanical scanning device and said detector means as a unit in a direction parallel to said vertical axis of rotation and relative to a human body to be examined; and means responsive to the signals which are produced by said elongated horizontal detector means as it is scanned by said pencil beam for generating images of the vertically oriented human body being examined on said support means; said drive means including means operative in a first mode to dispose said unit at a desired angle relative to said support means and to move said unit in translation generally parallel to the elongated vertical axis of rotation of said support means while said unit is maintained at said angle relative to said support means and while said support means is in a nonrotating condition, thereby to produce a localization image representative of a vertical axial section of the human body being examined, and said drive means including means operative in a second mode to position said unit translationally relative to said support means to a predetermined position adjacent a particular cross-sectional portion of interest of the human body being examined, selected by reference to said localization image, and to rotate said support means and the human body thereon smoothly and continuously about said vertically oriented axis of rotation while said unit is held stationary at said predetermined position thereby to produce in said second mode of operation an image representative of a horizontal slice of the human body being examined at the cross-sectional portion of interest selected by reference to the localization image produced during said first mode of operation.

2. The radiant energy imaging apparatus to claim 1 wherein said X-ray system is operative to expose said body to a total X-ray dosage of substantially 100 mR during a complete rotation of said body to be examined.

3. The radiant energy imaging apparatus of claim 1 wherein a plurality of elongated detectors are disposed horizontally in side-by-side parallel relation to one another, said pencil beam of X-rays impinging on said plurality of detectors simultaneously, whereby said plurality of detectors simultaneously produce output signals representative respectively of the X-ray response of adjacent cross-sectional slices of the body to be examined as said drive means rotates said human body about said vertically oriented axis of rotation.

4. The radiant energy imaging apparatus of claim 3 wherein said pencil beam of X-rays has a cross section which is elongated in a direction transverse to the directions of elongation of said side-by-side detectors, said pencil beam being scanned respectively from a position adjacent first corresponding ends of said elongated detectors to a position adjacent the opposite corresponding ends of said elongated detectors along a scan path which is transverse to the direction of elongation of said beam.

5. The radiant energy imaging apparatus of claim 3 wherein at least some of said elongated detectors are contiguous with one another, and means for combining the output signals produced by at least two contiguous ones of said detectors for adjusting the width of the cross-sectional slice which is being examined in said body.

6. The method of examining a human body by means of penetrating radiation, comprising the steps of supporting a human body to be examined along a vertically oriented axis, moving an X-ray unit translationally as a unit in a vertical direction parallel to said axis while said human body is held stationary along said vertically oriented axis, said X-ray unit comprising a source of X-rays located on one side of said axis and a single elongated radiant energy detector oriented horizontally and located on the other side of said axis, said detector being interconnected to said source for movement therewith in said vertical direction and being responsive to X-rays which are radiated by said source in a horizontal plane and which pass through a vertically oriented human body supported along said axis for producing a first series of detector output signals representative of the X-ray opacity of a vertical axial section of the human body being examined, converting said first series of signals into a visible localization image of said vertical axial section of the human body, selecting a particular horizontally oriented cross-section portion of interest of the human body being examined by reference to said localization image, moving said X-ray unit translationally in said vertical direction to a selected vertical position adjacent said axis wherein said horizontal plane passes through said particular horizontal cross-sectional portion of interest of the human body being examined, smoothly and continuously rotating said human body about said vertically oriented axis while said X-ray unit is held stationary at said selected vertical position whereby said detector products a second series of output signals representative of the X-ray opacity of said particular horizontal cross-sectional portion of the human body being examined, and converting said second series of output signals into a visible image of said horizontal cross-sectional portion of the human body being examined.

7. The method of claim 6 wherein said X-ray unit is operative to produce a single pencil beam of X-rays, said method including the step of sweeping said pencil beam through said horizontal plane to a succession of horizontally displaced positions along said horizontally oriented detector during the production of each of said first and second series of detector output signals.

* * * * *